United States Patent [19]

Lievense et al.

[11] Patent Number: 4,840,898

[45] Date of Patent: Jun. 20, 1989

[54] HIGH TEMPERATURE METHOD FOR THE PRODUCTION OF RIBAVIRIN

[75] Inventors: Jefferson C. Lievense, Rochester, N.Y.; Joanna D. Sawyer, Littleton, Colo.; Anthony J. Terpolilli, Rochester, N.Y.

[73] Assignee: Eastman Kodak Company, Rochester, N.Y.

[21] Appl. No.: 97,762

[22] Filed: Sep. 17, 1987

[51] Int. Cl.$^4$ .................. C12P 19/38; C12P 19/28; C12R 1/13
[52] U.S. Cl. ........................ 435/87; 435/85; 435/840
[58] Field of Search .............. 435/85, 840, 87

[56] References Cited

U.S. PATENT DOCUMENTS

| | | | |
|---|---|---|---|
| 3,976,545 | 8/1976 | Witkowski et al. | 195/28 |
| 4,458,016 | 7/1984 | Yamanaka et al. | 435/85 |
| 4,614,719 | 9/1986 | Fujishima et al. | 435/85 |

OTHER PUBLICATIONS

Derwent Abs. 77-76390Y/43 (J50123883) (9-1975) Kyowa.
Derwent Abs. 84-29121S/42 (J59179094) (10-1984) Yamasa.
Biotech 88-11277 (J63177797) (7-1988).
Biotech 88-05074 (Agrig. Biol. Chem.) (1988) 52,1,295-296.
Biotech 88-10183 Agrig. Biol. Chem. (1988) 52,7,1777-83.
Biotech 88-08418 Agrig. Biol. Chem. (1988) 52,5,1233-37.
U.S. Ser. No. 97,767, filed 9/17/87, Pochodylo.

*Primary Examiner*—Herbert J. Lilling
*Attorney, Agent, or Firm*—J. Jeffrey Hawley

[57] ABSTRACT

A method for the production of a 1,2,4-triazole nucleoside comprising the step of reacting a ribose donor with a triazole compound in the presence of an enzyme preparation derived from *Brevibacterium acetylicum* is disclosed. The method is characterized in that the ribose donor is guanosine and the temperature during at least a part of the reaction is at or above 65° C. The method is capable of high production rates and high concentrations of the final product.

5 Claims, No Drawings

HIGH TEMPERATURE METHOD FOR THE PRODUCTION OF RIBAVIRIN

BACKGROUND OF THE INVENTION

The present invention is directed to a method for the production of ribavirin and related compounds. The systematic name for ribavirin is 1-B-D-ribofuranosyl-1,2,4-triazole-3-carboxamide. Compounds of this type are known antiviral agents. Reference is made to U.S. Pat. No. 3,798,209 of Joseph T. Witkowski et al issued Mar. 19, 1974. Throughout the present specification, reference will be made to ribavirin. It will be understood that related compounds having a ribose group attached to a triazole are also intended.

There are several methods for the production of ribavirin. Chemical methods (those methods not using enzymes) are expensive. Expensive starting materials and process steps characterized by low yields are common.

As a result, bioconversion methods have been extensively studied. In these methods, an enzyme or enzymes are used to attach the ribose to the triazole. In some cases, the enzyme is first isolated and then used as the catalyst. Reference is made to U.S. Pat. No. 3,976,545 of Witkowski et al issued Aug. 24, 1976. In this patent there is disclosed a method wherein the ribose donor is ribose-1-phosphate. The triazole acceptor 1,2,4-triazole-3-carboxamide is reacted with the donor in the presence of nucleoside phosphorylase at a temperature between 0° C. and 50° C. The source of the enzyme is broadly disclosed.

Methods involving fermentation are also well known. In these methods the 1,2,4-triazole-3-carboxamide is added to a culture medium containing proliferating microorganisms such as a microorganism from the genus Brevibacterium. In this case, the necessary ribose donor comes from the fermentation medium as the organisms grow. Since the organisms are growing, the temperature is relatively low. Typical temperatures are between 20° C. and 40° C. Reaction times are very long, typically on the order of days.

In U.S. Pat. No. 4,458,016 to Yamanaka et al issued July 3, 1984 there is described a method that is very similar to the method of the U.S. Pat. No. 3,976,545 discussed above except that the temperature is between 55° and 65° C. Rather than isolated enzyme, whole cells containing the necessary activity can be used. Comparative results in the specification of this patent with the specific materials used indicate that the amount of ribavirin that is produced is very low at 70° C. and negligible at 75° C. and 80° C. (see table 3 at column 7) The microorganism that was used in this test was *Klebsiella pneuminiae* and the ribose donor was either ribose-1-phosphate or uridine.

In U.S. Pat. No. 4,614,719 to Fujishima et al issued Sept. 30, 1986 there is disclosed a method that is similar to the method of U.S. Pat. No. 4,458,016 discussed above. In U.S. Pat. No. 4,614,719 a *Brevibacterium acetylicum* microorganism is used under nonproliferative conditions. A wide variety of ribose donors can be used according to this disclosure and the temperature can be between 40° C. and 80° C. However, in the examples, inosine is predominantly used as the donor and the temperature is usually 60° C. In example 2 a variety of donors are tested with the *B. acetylicum* at 60° C. and in Example 4 a variety of temperatures up to 70° C. are tested with that microorganism and inosine as the donor. The yield of ribavirin dramatically decreases between 65° and 70° C.

The bioconversion method of U.S. Pat. No. 4,458,016 and U.S. Pats. No. 4,614,719 offer many advantages over the previous chemical method and the methods where the enzyme had to be isolated before use. However, additional improvements were still needed. For example, these methods produce ribavirin at a rate that is slower than desired. In U.S. Pat. No. 4,619,714 examples, the typical reaction time is 20 or 24 hours and the amount of ribavirin produced is relatively low. (Calculated to be at most about 10 g/L based on the data given.) Thus, while the % yield (actually the % conversion as described below) might be acceptable in these methods, the productivity of these methods is less than desired. Further, since the ribavirin is produced in only dilute solution, the recovery is more expensive than desired.

SUMMARY OF THE INVENTION

In accordance with the present invention there is provided an improved method for the production of a 1,2,4-triazole nucleoside comprising the step of reacting a ribose donor with a triazole compound in the presence of an enzyme preparation derived from *Brevibacterium acetylicum*. The improvement according to the present invention is that the ribose donor is guanosine or a guanosine derivative and the temperature during at least a part of the reaction is at or above 65° C. The method according to this invention is capable of achieving higher concentrations of the desired product in the reaction mixture.

In accordance with a further improvement, the initial concentration of the ribose donor and the triazole is greater than 100 mM. The highest concentration in the examples of U.S. Pat. No. 4,614,719 is about 50 mM. We have found that the present method is capable of utilizing the higher concentration because of the donor selected and the higher temperatures used.

At extremely high concentrations of the reactants, we have found that there is a tendency for the reaction mixture to gel. In a preferred embodiment of the invention, this problem is avoided by adding the enzyme preparation before gelling occurs.

In the typical method, the enzyme preparation is separated from the reaction mixture and discarded. We have found that significant amounts of the desired product are associated with the enzyme preparation. In a preferred embodiment of this invention, the enzyme preparation is separated from the reaction mixture and is washed so as to recover additional product.

In accordance with a further improvement of the method, there is provided the additional step of adding the ribose donor and the triazole during the course of the reaction. This method is capable of producing ribavirin and related compounds in very high concentrations.

DETAILED DESCRIPTION OF THE INVENTION

Through the use of a specific ribose donor we found that higer than usual temperatures could be used. The result is an increase in the productivity of the reaction with little or no decrease in the conversion. This result was surprising since the prior art suggested that the conversion decreased dramatically at higher temperatures. This was confirmed by comparative experiments described below. Using different donors, for example inosine, it was found that at a temperature of 70° C., the rate was not as high as desired nor was the conversion of the starting materials to the desired product as high as desired.

We have also found that not only is the initial rate higher, but the production of ribavirin continues at a high rate for an extended period thereby producing a high concentration of the desired product in the final reaction mixture. While not wishing to be bound by any particular theory, it may be that this occurs because the by-product of guanosine is less soluble than the by-product of other donors. Therefore, there could be less of a chance that the by-product inhibits the action of the enzyme. Therefore, the high rate of ribavirin production continues at a high level and high concentrations are attained.

The final concentration of the ribavirin in the reaction mixture is an important component of the overall cost of carrying out the method. High concentrations allow for better economics since the recovery from concentrated solutions is less expensive than from dilute solutions. Using the method of the present invention, very high ribavirin concentrations, on the order of 100 g/L in preferred embodiments, can easily be achieved.

In accordance with the present invention, the temperature should be at or above 65° C. during at least part of the method. Any temperature above this limit can be used but as a practical matter, the conversion does decrease as the temperature increases, even though the rate of production remains high. Thus, a temperature of about 70° C. is preferred.

The ribose donor is guanosine. It can be purchased commercially and is found in the hydrolysate of RNA, for example yeast RNA. Derivatives of guanosine can also be used such as guanylic acid.

The microorganism that is employed as the source of the catalytic activity is a *Brevibacterium acetylicum*. Any strain of this species can be used. The strain identified as ATCC 39311 available from the American Type Culture Collection and which is described in U.S. Pat. No. 4,614,719 referenced above is preferred.

The microorganism can be prepared by conventional fermentation processes such as the process described in Preparation 1 just prior to the present examples. A sample of the microorganism is inoculated into a fermentor with suitable nutrients and caused to grow to a stationary phase. The resulting fermentation broth can be used directly as the catalytic material. The cells can also be removed from the broth by filtration or centrifugation and used as a cell paste. The cells can be treated so as to increase their permeability. Treatments such as freeze thawing, and other treatments described in U.S. Pat. No. 4,614,719 are useful for this purpose.

According to the present invention any enzyme preparation that is derived from *B. acetylicum* is useful. This includes the preparations described above and also any preparations from microorganisms that express the gene or genes isolated from *B. acetylicum* that is responsible for the nucleoside phosphorylase activity of this microorganism.

The concentration of the reactants in the reaction mixture can vary widely. The concentration of the guanosine donor can be between about 10 mM and 500 mM; the triazole between about 10 mM and 500 mM; and the cells present in an amount of between about 2 g/L and 100 g/L based on the cell dry weight. Since the reaction uses one mole of donor for each mole of triazole, it is preferred that these reagents be in the reaction mixture in this ratio.

The starting pH can also vary widely and can range between about 6.0 and 9.2. While it is not critical to control the pH during the reaction, pH control is desirable. The optimum pH for ribavirin production is about 7.2.

In preferred methods according to the invention, the concentration of the starting materials is higher than that usually found in similar methods. For example, guanosine is preferably present in an amount of between 100 mM and 200 mM while the triazole is preferably present in an amount of between 100 mM and 200 mM.

We have found that reaction mixtures using the donor guanosine tend to gel at high concentrations of guanosine at relatively high temperatures. Accordingly, it is preferred according to the present invention to add the catalyst before gelling occurs. Thus, the catalyst can be first mixed with one of the reagents and the other of the reagents added to that mixture. As the other reagent is added, the reaction begins immediately thereby preventing gel formation. Alternatively, the reactants can be mixed at low temperature and the catalyst added as the temperature is increased but before gelling occurs. These procedures are not suggested in the references cited above. In U.S. Pat. No. 4,614,719, for example, the reagent mixture is first formed and the catalyst is added to that mixture.

In a particularly preferred embodiment, ribose donor and triazole are added during the course of the reaction. These reagents can be added continuously or in batches over time for example, every eight hours. The rate of addition is preferably about 40 mM/hour although higher and lower rates can be used. As noted previously, concentrations of ribavirin near 100 g/L can be achieved over the course of the reaction. Depending on the desired ending concentration, the time of reaction can vary widely, for example between about 6 to 30 hours.

In addition to the ribose donor and the triazole, the reaction mixture preferably contains phosphate ion as this may be required by the enzymes. A useful source of phosphate ions is potassium monophosphate and the concentration is typically between about 25 mM and 100 mM. Lower levels of phosphate are useful if the pH is controlled during the reaction.

In conventional methods of the present type, the cells that are used as the catalyst are removed from the reaction mixture and discarded. We have found that these cells contain a significant amount of the desired product. Thus, in a preferred method, the enzyme preparation is recovered, such as by centrifugation and washed. Additional product is then recovered from the wash liquid. The wash liquid is preferably water.

In the examples below, the % conversion is referred to. The % conversion is the amount of ribavirin, on a molar basis, divided by the initial amount of starting materials, based on the molar amount of the limiting reactant. This is believed to be referred to as yield in the prior art art references. More precisely, yield refers to the amount of product produced divided by the amount of starting material that reacts. To calculate yield, the final amount of starting material must be known. In the present examples, no effort was made to measure the remaining amount of starting material at the end of the reaction. If the starting materials go only to the desired product, then % conversion and % yield are the same.

The following preparation and examples are submitted for a further understanding of the invention.

PREPARATION 1

Preparation of: Brevibacterium acetylicum

Ten liters of an aqueous cultivation medium at pH 7.2 was prepared, sterilized, and combined in a fermentor. The composition of the medium is shown in Table I. An inoculum was prepared by culturing *Brevibacterium acetylicum* ATCC 39311 in a Fernbach flask containing 500 mL of medium for 20 hours at 30° C. The Fernbach medium was identical to that used in the fermentor, except it lacked magnesium sulfate. After transfer of the inoculum, the fermentor was cultured at 30° C. for 20 hours. The pH was controlled at 7.2 with potassium hydroxide. Additional glucose, amounting to 20 g/L of broth, was added at 12 hours into the fermentation.

At the end of the fermentation, centrifugation of the broth yielded 50 grams of wet cells per liter of broth. The cells were washed by re-suspending them in a 10mM Phosphate buffer. They were then collected by centrifugation and stored as a frozen paste.

TABLE I

Fermentation Medium

| Component | Concentration (g/L) |
|---|---|
| 1. Nutrient broth | 20 |
| 2. $K_2HPO_4$ | 14 |
| 3. $KH_2PO_4$ | 5.5 |
| 4. Sodium citrate | 0.025 |
| 5. $MnCl_2 \cdot 4H_2O$ | 0.015 |
| 6. $ZnCl_2$ | 0.01 |
| 7. $FeCl_3 \cdot 6H_2O$ | 0.01 |
| 8. $MgCl_2 \cdot 6H_2O$ | 0.25 |
| 9. $CuCl_2 \cdot 2H_2O$ | 0.001 |
| 10. $CaCl_2 \cdot 2H_2O$ | 0.00375 |
| 11. $CoCl_2 \cdot 2H_2O$ | 0.001 |
| 12. $NaMoO_4 \cdot 2H_2O$ | 0.0005 |
| 13. Polyglycol P-2000* | 2 |
| 14. Glucose | 50 |
| 15. $MgSO_4 \cdot 7H_2O$ | 0.75 |
| 16. Thiamine·HCl | 0.0002 |
| 17. p-Aminobenzoic acid | 0.0002 |
| 18. Pyridoxine·HCl | 0.0002 |
| 19. Nicotinic acid | 0.0002 |
| 20 Riboflavin | 0.0002 |
| 21. Calcium d-pantothenate | 0.0002 |
| 22. Folic acid | 0.000002 |

*available from Dow Chemical Midland Mich. USA

EXAMPLE 1

Performance of the Bioconversion as a Function of Temperature and pH using Guanosine as the Ribose Donor Bioconversion media were prepared by combining 20 millimoles of guanosine, 20 millimoles of 1,2,4-triazole-3-carboxamide, and 20 millimoles of $KH_2PO_4$ with 200 mL water in 500 mL flasks. The pH of each flask was adjusted to the desired value with potassium hydroxide or sulfuric acid.

The flasks were placed in temperature-controlled baths, and the contents of the flasks were allowed to equilibrate at the desired temperature. Forty grams of *B. acetylicum* cell paste (thawed at room temperature) were then added to each flask to initiate the bioconversion. The contents of the flasks were stirred via a magnetic stirrer.

Samples were removed periodically from the bioconversion mixtures for analysis of the ribavirin concentration. The concentration in the cell-free solution was determined. The initial reaction rate calculated over the first hour of the bioconversion, the cell-free ribavirin concentration and conversion after seven hours of reaction, and the final, cell-free ribavirin concentration and conversion (measured after 20 to 27 hours) are shown in Table II as a function of the reaction temperature and initial reaction pH. The conversion is expressed on a molar basis with respect to the initial concentration of guanosine in the cell-free solution.

TABLE II

Ribavirin Production as a Function of Temperature and pH with Guanosine as the Ribose Donor

| Initial pH | Temp. (°C.) | Initial Rate of Ribavirin Production (g/L/Hr.) | Ribavirin Conc. (g/L) 7 Hr. | Final | % Conversion 7 Hr. | Final |
|---|---|---|---|---|---|---|
| 6.0 | 65 | 1.1 | 12.8 | 16.4 | 52 | 67 |
|  | 70 | 1.0 | 6.8 | 7.8 | 28 | 68 |
|  | 75 | 0.3 | 0.3 | 4.0 | 1 | 1 |
| 6.8 | 65 | 2.8 | 14.0 | 16.8 | 57 | 69 |
|  | 70 | 2.6 | 16.6 | 17.2 | 68 | 70 |
|  | 75 | 2.8 | 4.0 | 4.0 | 16 | 16 |
| 7.6 | 65 | 3.5 | 10.6 | 14.5 | 43 | 59 |
|  | 70 | 4.6 | 15.0 | 16.8 | 61 | 69 |
|  | 75 | 4.1 | 6.4 | 7.0 | 26 | 29 |
| 8.4 | 65 | 3.7 | 14.2 | 17.0 | 58 | 70 |
|  | 70 | 4.6 | 14.6 | 16.0 | 60 | 66 |
|  | 75 | 3.3 | 6.0 | 6.0 | 25 | 25 |
| 9.2 | 65 | 3.2 | 14.0 | 16.5 | 57 | 68 |
|  | 70 | 3.8 | 11.4 | 14.2 | 47 | 58 |
|  | 75 | 2.4 | 3.2 | 3.0 | 13 | 12 |

EXAMPLE 2

Comparison of Bioconversion Performance Using Various Nucleosides at 70° C. and pH 7.2

Bioconversion mixtures were prepared as in Example 1, except that the ribose donor was varied. Bioconversions were tested using five different nucleosides. All bioconversions were operated at 70° C. and an initial pH of 7.2. The results are given in Table III. The conversion is expressed on a molar basis with respect to the initial concentration of nucleoside in the cell-free solution. The final conversion was determined at 28.25 hours.

TABLE III

Ribavirin Production as a Function of Ribose Donor

| Ribose Donor | Initial Rate of Ribavirin Production (g/L/Hr.) | Ribavirin Conc. (g/L) 6.5 Hr. | Final | % Conversion 6.5 Hr. | Final |
|---|---|---|---|---|---|
| Adenosine* | 5.6 | 7.4 | 9.6 | 30 | 39 |
| Guanosine | 4.3 | 16.2 | 18.1 | 66 | 74 |
| Inosine* | 1.4 | 5.7 | 10.3 | 23 | 42 |
| Cytidine* | 0 | 0 | 0 | 0 | 0 |
| Uridine* | 2.3 | 2.3 | 2.3 | 9 | 9 |

*Comparison

EXAMPLE 3

Gel Prevention and Cell Washing (A) Comparison

Bioconversion media were prepared as in Example 1, except the amounts of guanosine and 1,2,4-triazole-3-carboxamide were 20, 40, or 100 millimoles. The two reactants were used in a 1:1 molar ratio. The initial pH of each flask was adjusted to pH 7.2 with potassium hydroxide.

The flask with 100 millimoles of the two reactants gelled as it was heated to 70° C.—before any cell paste was added. The flask with 40 millimoles of the two reactants also gelled, but required a few minutes longer. Agitation via the stir bar was ineffective in reversing the gelling in both cases.

(B)

Bioconversion media were prepared as in Example 1, except the amounts of guanosine and 1,2,4-triazole-3-carboxamide were varied from 20 to 40 millimoles. The two reactants were used in a 1:1 molar ratio. The initial pH of each flask was adjusted to pH 7.2 with potassium hydroxide. The bioconversions were initiated and operated as in Example 1, except that the temperature was 70° C. The cells were added promptly as the temperature reached 70° C. to avoid gelling of the bioconversion mixture.

The final conversion was determined at 24 hours. Each bioconversion broth was centrifuged, and samples were taken from the supernatant for determination of the final, cell-free ribavirin concentration.

The cell paste from each bioconversion (about 40 grams) was re-suspended in 200 mL water. These solutions were stirred at 22° C. for 1 hour to extract ribavirin from the cells. The solutions were then centrifuged, and samples were taken from the supernatant for determination of the extracted ribavirin. The extraction process was repeated a second time using fresh water and the cell paste from the first extraction.

The initial reaction rate calculated over the first hour of the bioconversion, the cell-free ribavirin concentration and conversion after seven hours of reaction, and the final, cell-free ribavirin concentration and conversion, are shown in Table V as a function of the initial guanosine concentration in the cell-free solution. The increase in the final conversion obtained by extracting ribavirin from the cells is shown in Table VI.

TABLE V

Ribavirin Production as a Function of Initial Guanosine and 1,2,4-triazole-3-carboxamide Concentrations Between 100 and 200 mM

| Initial Guanosine Concen. (mM) | Initial Rate of Ribavirin Production (g/L/Hr.) | Ribavirin Conc. (g/L) 7 Hr. | Ribavirin Conc. (g/L) Final | % Conversion 7 Hr. | % Conversion Final |
|---|---|---|---|---|---|
| 100 | 3.9 | 14.8 | 16.8 | 61 | 70 |
| 125 | 4.5 | 18.8 | 20.9 | 62 | 70 |
| 150 | 5.4 | 22.7 | 25.1 | 62 | 70 |
| 175 | 5.4 | 25.7 | 28.9 | 60 | 68 |
| 200 | 5.5 | 28.3 | 32.8 | 58 | 68 |

TABLE VI

Impact of Extraction of Ribavirin from Cells on the Final Conversion

| Initial Guanosine Concen. (mM) | Final Conversion (%) No Extraction | Final Conversion (%) One Extraction | Final Conversion (%) Two Extractions |
|---|---|---|---|
| 100 | 70 | 78 | 79 |
| 125 | 70 | 79 | 80 |
| 150 | 70 | 79 | 80 |
| 175 | 68 | 77 | 78 |
| 200 | 68 | 77 | 79 |

EXAMPLE 4

Accumulation of Ribavirin to a High Concentration Using a Fedbatch Bioconversion Bioconversion media were prepared as in Example 1, except the initial amounts of guanosine and 1,2,4-triazole-3-carboxamide were 40 millimoles. The initial pH of each flask was adjusted to pH 7.2 with potassium hydroxide. The bioconversions were initiated as in Example 1, except that the temperature was 70° C. The cells were added promptly as the temperature reached 70° C. to avoid gelling of the bioconversion mixture. Forty millimole additions of both guanosine and 1,2,4-triazole-3-carboxamide were made at 6 and 12 hours into the bioconversion. Thus after the second addition, a total of 120 millimoles of the two reactants had been added. Potassium hydroxide was added at 6 hours to adjust the pH from 6.7 to 7.2.

The cell-free ribavirin concentration, the conversion based on guanosine, and the overall reaction rate at 6, 12, and 24 hours are shown in Table VII.

TABLE VII

Performance of the Fed-batch Bioconversion

| Time (Hrs) | Ribavirin Conc. (g/L) | Average Production Rate (g/L/Hr.) | % Conversion |
|---|---|---|---|
| 0 | 0 | 0 | 0 |
| 6 | 25.8 | 4.3 | 53 |
| 12 | 56.7 | 4.7 | 58 |
| 24 | 94.9 | 4.0 | 65 |

EXAMPLE 5 Batch Conversion with 500 mM Guanosine and 1,2,4-triazole-3-carboxamide A bioconversion medium was prepared by combining 10 millimoles of guanosine and 10 millimoles of 1,2,4-triazole-3-carboxamide with 10 millimoles of $KH_2PO_4$ in 100 mL of water in a 500 mL flask at 70° C. Forty grams of cell paste were then added, followed next by 90 millimoles of guanosine and 90 milimoles of 1,2,4-triazole-3-carboxamide and finally by 10 millimoles of $KH_2PO_4$ in 100 mL water at room temperature. The reaction mixture was vigorously stirred during this preparation with a top-driven laboratory stirrer.

The resulting reaction mixture was of a pasty consistency but did not gel. Production of ribavirin was similar to that of Example 4.

The invention has been described in detail with particular reference to preferred embodiments thereof, but it will be understood that variations and modifications can be effected within the spirit and scope of the invention.

We claim:

1. In a method for the production of a 1,2,4-triazole nucleoside comprising the step of reacting a ribose donor with a triazole compound in the presence of an enzyme preparation derived from *Brevibacterium acetylicum,* the improvement wherein the ribose donor is guanosine or a guanosine derivative and the temperature during at least a part of the reaction is at or above 65° C. so that the precent conversion of starting materials to the 1,2,4-triazole nucleoside is greater than about 58 percent.

2. The method according to claim 1 wherein the temperature is about 70° C.

3. The method according to claim 1 wherein the enzyme preparation comprises cells of *Brevibacterium acetylicum.*

4. The method according to claim 1 wherein said triazole compound is 1,2,4-triazole-3-carboxamide.

5. The method according to claim 1 wherein said 1,2,4-triazole nucleoside is 1-B-D-ribofuranosyl-1,2,4-triazole-3-carboxamide.

* * * * *